US011992279B2

United States Patent
Liu et al.

(10) Patent No.: US 11,992,279 B2
(45) Date of Patent: May 28, 2024

(54) PROXIMITY SENSORS FOR SURGICAL ROBOTIC ARM MANIPULATION

(71) Applicant: Verb Surgical Inc., Santa Clara, CA (US)

(72) Inventors: Xin Liu, Milpitas, CA (US); Berk Gonenc, Cupertino, CA (US); Bernhard A. Fuerst, Sunnyvale, CA (US); Jose Luis Cordoba, Malaga (ES); Pablo E. Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 17/961,459

(22) Filed: Oct. 6, 2022

(65) Prior Publication Data

US 2023/0107307 A1 Apr. 6, 2023

Related U.S. Application Data

(63) Continuation of application No. 16/418,693, filed on May 21, 2019, now Pat. No. 11,504,193.

(51) Int. Cl.
*B25J 9/16* (2006.01)
*A61B 34/30* (2016.01)
(Continued)

(52) U.S. Cl.
CPC ............ *A61B 34/30* (2016.02); *B25J 9/1676* (2013.01); *B25J 9/1694* (2013.01); *B25J 13/086* (2013.01);
(Continued)

(58) Field of Classification Search
CPC .......... A61B 34/30; A61B 2017/00119; A61B 2017/00199; A61B 2017/00398;
(Continued)

(56) References Cited

U.S. PATENT DOCUMENTS

| 7,570,064 B2 | 8/2009 | Roziere |
| 8,269,176 B2 | 9/2012 | D'Ambrosio et al. |

(Continued)

FOREIGN PATENT DOCUMENTS

| CN | 101227870 A | 7/2008 |
| CN | 101627320 A | 1/2010 |

(Continued)

OTHER PUBLICATIONS

Feasibility of touch-less control of operating room lights, by Florian Harmann and Alexander Schlaefer; International Journal of Computer Assisted Radiology and Surgery; vol. 8, Issue 2, pp. 259-268; Mar. 2013.

(Continued)

*Primary Examiner* — Sohana Tanju Khayer
(74) *Attorney, Agent, or Firm* — Aikin & Gallant, LLP (57) ABSTRACT

A surgical robotic system including a surgical table, a surgical robotic manipulator coupled to the surgical table and comprising a plurality of links coupled together by a plurality of joints that are operable to move with respect to one another to move the surgical robotic manipulator, at least one of the plurality of links or the plurality of joints having a portion that faces another of the plurality of links or the plurality of joints, a proximity sensing assembly coupled to the portion of the at least one of the plurality of links or the plurality of joints, the proximity sensing assembly operable to detect an object prior to the surgical robotic manipulator colliding with the object and to output a corresponding detection signal, and a processor operable to receive the corresponding detecting signal and cause the manipulator or the object to engage in a collision avoidance operation.

19 Claims, 7 Drawing Sheets

(51) Int. Cl.
*B25J 13/08* (2006.01)
*A61B 17/00* (2006.01)
*A61B 34/20* (2016.01)
*A61B 90/00* (2016.01)

(52) U.S. Cl.
CPC ............ *A61B 2017/00119* (2013.01); *A61B 2017/00199* (2013.01); *A61B 2017/00398* (2013.01); *A61B 2034/2051* (2016.02); *A61B 2090/061* (2016.02); *A61B 2562/0257* (2013.01)

(58) Field of Classification Search
CPC ...... A61B 2034/2051; A61B 2090/061; A61B 2562/0257; B25J 9/1676; B25J 9/1694; B25J 13/086
See application file for complete search history.

(56) References Cited

U.S. PATENT DOCUMENTS

| | | |
|---|---|---|
| 8,816,628 B2 | 8/2014 | Nowlin et al. |
| 9,323,398 B2 | 4/2016 | Bernstein et al. |
| 9,579,793 B2 | 2/2017 | Jacob et al. |
| 9,914,211 B2 | 3/2018 | Hynna et al. |
| 10,022,195 B2 | 7/2018 | Scholan |
| 11,278,361 B2 | 3/2022 | Gonenc |
| 11,504,193 B2 | 11/2022 | Liu et al. |
| 2003/0208303 A1 | 11/2003 | Okamoto et al. |
| 2007/0013336 A1* | 1/2007 | Nowlin ............ A61B 34/77 318/568.21 |
| 2010/0061509 A1 | 3/2010 | D'Ambrosio et al. |
| 2012/0215351 A1* | 8/2012 | McGee ............ B25J 9/1676 700/248 |
| 2013/0244731 A1 | 9/2013 | Oishi et al. |
| 2013/0325029 A1 | 12/2013 | Hourtash et al. |
| 2014/0130810 A1* | 5/2014 | Azizian ............ A61B 46/10 128/849 |
| 2015/0038981 A1 | 2/2015 | Kilroy et al. |
| 2015/0038982 A1 | 2/2015 | Kilroy et al. |
| 2016/0089175 A1 | 3/2016 | Hibner et al. |
| 2016/0270867 A1 | 9/2016 | Scholan |
| 2017/0086928 A1 | 3/2017 | Auld et al. |
| 2017/0168567 A1 | 6/2017 | Reese et al. |
| 2017/0215975 A1 | 8/2017 | Nowlin et al. |
| 2017/0252921 A1* | 9/2017 | Hynna ............ A61B 17/00234 |
| 2017/0258534 A1 | 9/2017 | Hourtash et al. |
| 2017/0296277 A1 | 10/2017 | Hourtash et al. |
| 2018/0078319 A1 | 3/2018 | Nobles et al. |
| 2018/0092706 A1 | 4/2018 | Anderson et al. |
| 2018/0161108 A1 | 6/2018 | Savall et al. |
| 2018/0177523 A1* | 6/2018 | Piron ............ A61B 5/0062 |
| 2018/0288515 A1 | 10/2018 | Peterson et al. |
| 2018/0296857 A1* | 10/2018 | Robar ............ A61N 7/02 |
| 2018/0311814 A1 | 11/2018 | Kamisono et al. |
| 2018/0344559 A1 | 12/2018 | Hoel et al. |
| 2019/0000569 A1* | 1/2019 | Crawford ............ A61B 34/20 |
| 2019/0001501 A1 | 1/2019 | Roberts |
| 2019/0005848 A1 | 1/2019 | Garcia Kilroy et al. |
| 2019/0008367 A1 | 1/2019 | Ishikawa et al. |
| 2019/0031300 A1* | 1/2019 | Bangslund ............ B63B 35/00 |
| 2019/0063907 A1* | 2/2019 | Grau ............ G06T 7/521 |
| 2019/0111945 A1 | 4/2019 | Wiegand et al. |
| 2019/0216555 A1* | 7/2019 | DiMaio ............ A61B 34/00 |
| 2019/0228859 A1 | 7/2019 | Moctezuma de la Barrera |
| 2019/0358815 A1 | 11/2019 | Nakayama et al. |
| 2020/0078097 A1* | 3/2020 | Gregerson ............ A61B 5/1127 |
| 2020/0164516 A1* | 5/2020 | Lehment ............ B25J 9/1676 |
| 2020/0253678 A1* | 8/2020 | Hulford ............ A61B 90/30 |
| 2021/0178605 A1* | 6/2021 | Shigetaka ............ G01V 3/08 |
| 2022/0018096 A1* | 1/2022 | Nishi ............ G06N 3/045 |
| 2022/0387131 A1 | 12/2022 | Anderson et al. |

FOREIGN PATENT DOCUMENTS

| | | |
|---|---|---|
| CN | 106293293 A | 1/2017 |
| CN | 106725860 A | 5/2017 |
| CN | 107532878 A | 1/2018 |
| EP | 1324364 | 2/2003 |
| WO | WO2006124390 | 11/2006 |
| WO | 2012/044334 A2 | 4/2012 |
| WO | WO2016020052 | 2/2016 |
| WO | WO2016082019 | 6/2016 |
| WO | WO2018052795 | 3/2018 |
| WO | WO2018148845 | 8/2018 |

OTHER PUBLICATIONS

Thracker—Using Capacitive Sensing for Gesture Recognition, by Raphael Wimmer, Paul Holleis, Matthias Kranz, Albrecht Schmidt; Proceedings of the 26th IEEE International Conference on Distributed Computing Systems Workshops (ICDCSW'06) 0-7695-2541-5 /06: 2006: 6 pages.
A Capacitance Based Proximity Sensor for Whole Arm Obstacle Avoidance, by J. L Novak and J. T. Feddema; Proceedings 1992 IEEE International Conference on Robotics and Automation; 1992; 23 Pages.
International Search Report & Written Opinion of the International Searching Authority dated Feb. 18th, 2020, for PCT application No. US2019/034718.
International Search Report and Written Opinion of the PCT Patent Office dated Feb. 18, 2020 for related PCT Patent Application No. PCT/US2019/034719.
International Preliminary Report on Patentability for International Application No. PCT/US2019/034718 dated Dec. 2, 2021, 9 pages.
International Preliminary Report on Patentability for International Application No. PCT/US2019/034719 dated Dec. 2, 2021, 9 pages.
International Search Report & Written Opinion of the International Searching Authority dated Feb. 18, 2020, for PCT application No. US2019/034718.
Office Action received for Chinese Patent Application No. 201980096609.4, dated Oct. 27, 2023, 18 pages (9 pages of English Translation and 9 pages of Original Document).
Office Action received for Chinese Patent Application No. 201980096677.0, mailed on Jan. 30, 2024, 21 pages (10 pages of English Translation and 11 pages of Original Document).
Office Action received for Korean Patent Application No. 10-2021-7040826, mailed on Feb. 26, 2024, 20 pages (9 pages of English Translation and 11 pages of Original Document).
Office Action received for Korean Patent Application No. 10-2021-7041467, mailed on Feb. 26, 2024, 15 pages (7 pages of English Translation and 8 pages of Original Document).

* cited by examiner

PROXIMITY SENSORS FOR SURGICAL ROBOTIC ARM MANIPULATION

CROSS-REFERENCE TO RELATED APPLICATIONS

The application is a continuation of pending U.S. application Ser. No. 16/418,693 filed May 21, 2019, which is incorporated in its entirety.

BACKGROUND

Field

Embodiments related to robotic systems, are disclosed. More particularly, embodiments related to surgical robotic arms and proximity sensors for collision avoidance, are disclosed.

Background

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted components and tools. For example, a surgical robotic system may include a number of surgical robotic manipulators, including surgical robotic arms, what are mounted to a surgical table and manipulated to perform surgical procedures. It is important, however, that during manipulation of the surgical robotic arms they do not collide with the various components within the surgical arena in which they are used.

SUMMARY

A surgical robotic system may include a surgical robotic manipulator, for example a surgical robotic arm, including a number of links which are connected to one another by joints. It is imperative that the surgical robotic arm and associated joints be capable of fluid motion and easily controlled. In addition, it is important that the robotic arm, during movement, is prevented from, for example, pinching the user and colliding with another object (e.g, another surgical robotic arm, surgical robotic arm link, an assistant, a patient, etc). To avoid and/or prevent collisions, the surgical robotic system disclosed herein includes capacitive hover sensors incorporated into the surgical robotic component, specifically the surgical robotic arm, at strategic locations determined to be susceptible to collision or critical to detecting a collision before it occurs. For example, the capacitive hover sensors may be located at one or more portions of the surgical robotic arm which allow for detection of an object such as a hand or finger that is about to be pinched between links making up a surgical robotic arm and/or an object such as another surgical robotic arm or surgical table that is about to be hit by the surgical robotic arm.

In one aspect, it is contemplated that the capacitive hover sensors may be sensors which can detect the presence, position and/or orientation of objects with respect to the sensor using capacitive sensing principles and prior to the object contacting the sensor. For example, conductive sensing pads may be attached to different positions of the surgical robotic arm in various configurations. When a pad is excited by a voltage source, the pad creates an electrical field around it. When a conductive object approaches the pad, it interferes with the field and forms/changes the capacitance of the pad. By monitoring the changes of the capacitance of different pads, the position and orientation of the object can be detected.

One or more capacitive hover sensors may be mounted on a portion of the surgical robotic arm, for example, on a surface of one or more links or joints of the surgical robotic arm. The sensors may be mounted so that the surgical robotic arm can detect if another surgical robotic arm is closing in and then respond to the potential collision by stopping its own movement and/or trigger an alarm. For example, the capacitive hover sensors may be mounted on one or more links (e.g., adjacent links) making up the surgical robotic arm at locations which can detect when a user's finger or hand is between two links which are closing in towards each other. The surgical robotic system can, in turn, engage in collision prevention or avoidance operations to prevent pinching of the hand or finger between the links. For example, the surgical robotic system may cause the surgical robotic arm to stop movement, manipulate one or more of the links to avoid pinching or trigger an alarm so the user moves their hand or finger out of the way. In other cases, the capacitive hover sensor may detect a nearby object such as another surgical robotic arm, table surface, body of the patient or staff, etc, and respond to prevent potential collisions. In some cases, the surgical robotic system may determine the type of object the surgical robotic arm is about to collide with and initiate collision avoidance and/or prevention operations depending on the type of object. Still further, users of the surgical robotic arm may configure the sensing range, sensing area or other sensitivity parameters of the sensing assembly to the desired level to avoid false negatives and false positive detections.

Representatively, in one aspect, a surgical robotic system includes a surgical table, a surgical robotic manipulator, a proximity sensor and a processor. The surgical robotic manipulator may be coupled to the surgical table and include a plurality of links coupled together by a plurality of joints that are operable to move with respect to one another to move the surgical robotic manipulator, at least one of the plurality of links or the plurality of joints having a portion that faces another of the plurality of links or the plurality of joints when moving the surgical robotic manipulator. The proximity sensor may be attached to the portion of the at least one of the plurality of links or the plurality of joints and be operable to detect an object prior to the surgical robotic manipulator colliding with the object and to output a corresponding detection signal. The processor may be operable to receive the corresponding detecting signal and cause the surgical robotic manipulator or the object to engage in a collision avoidance operation. In some aspects, the surgical robotic manipulator may include a surgical robotic arm and the proximity sensor is a capacitive hover sensing assembly coupled to a curved portion of at least one of the plurality of links or the plurality of joints that faces the surgical table when the surgical robotic arm is performing a surgical procedure. In some aspects, the surgical robotic manipulator may include a surgical robotic arm, the plurality of links coupled together by the plurality of joints comprises a first link and a second link coupled together by a pivot joint, and the proximity sensor is coupled to a portion of the first link which faces the second link when the first link or the second link pivots about the pivot joint. The surgical robotic manipulator may include a surgical robotic arm, and the portion is a portion of a joint that it is between at least two links of the plurality of links and the portion faces at least one of the links when the surgical robotic arm is moving. In still further aspects, the surgical robotic manipulator may be a tool drive coupled to a surgical robotic arm, and the proximity sensor is coupled to the tool drive. The tool drive may include a proximal portion and a distal portion, the distal portion being farther from the surgical table than a proximal portion during a surgical procedure, and the proximity sensor is coupled to the proximal portion. The proximity sensor may include a plurality of capacitive pads arranged in a pattern, and the plurality of capacitive pads detect a proximity of the object to the surgical robotic manipulator based on a change in capacitance at one or more of the capacitive pads. The proximity sensor may be operable to detect a proximity of the object to the surgical robotic manipulator and the object type, and based on the proximity and the object type, the processor determines the collision avoidance operation. The processor may cause the surgical robotic manipulator to engage in the collision avoidance operation, and the collision avoidance operation comprises terminating a movement of the surgical robotic manipulator. The processor may cause the object to engage in the collision avoidance operation, and the collision avoidance operation comprises moving the object so it is not in a pathway of movement of the surgical robotic manipulator. The processor is further operable to initiate an alarm alerting the user of an imminent collision based on the detection signal.

In another aspect, a collision avoidance method for a surgical robotic manipulator may include detecting a distance of an object to a surgical robotic manipulator using a proximity sensing assembly, wherein the surgical robotic manipulator comprises a plurality of links coupled together by a plurality of joints that are operable to move with respect to one another to move the surgical robotic manipulator and the proximity sensing assembly is coupled to a portion of at least one of the plurality of links that faces another link of the plurality of links when the surgical robotic manipulator is moving. The method further includes determining whether a collision between the object and the surgical robotic manipulator is imminent by comparing the detected distance of the object to a predetermined collision avoidance distance, the predetermined collision avoidance distance corresponding to a predetermined distance to be maintained between the object and the surgical robotic manipulator to avoid a collision. In addition, based on the determining, the method causes the surgical robotic manipulator or the object to engage in a collision avoidance operation that prevents the surgical robotic manipulator from colliding with the object. In some aspects, based on the determining , the surgical robotic manipulator is caused to engage in the collision avoidance operation, and wherein the collision avoidance operation comprises terminating movement of the surgical robotic manipulator. In some aspects, the method further includes detecting an object type using the proximity sensing assembly, and based on the distance of the object and the object type, determining a collision avoidance operation. The collision avoidance operation may include terminating movement of the surgical robotic manipulator when the object type is a person or causing a movement of the object when the object type is another surgical robotic manipulator. The predetermined collision avoidance distance may be different depending on the object type. The method may further include determining a location of the object with respect to a particular one of the plurality of links coupled together by a plurality of joints using the proximity sensing assembly, and based on the distance of the object and the location of the object to the surgical robotic manipulator, determining the collision avoidance operation. In some aspects, at least one of the plurality of links is operable to move in a first direction, and the proximity sensing assembly is coupled to a curved portion of the at least one of the plurality of links that faces the first direction. In still further aspects, the surgical robotic manipulator comprises a surgical robotic arm comprising at least seven links and at least seven joints that cause the at least seven links to move with respect to one another, and the proximity sensing assembly is coupled to a portion of a first link that faces a second link when the first link pivots about a first joint. The surgical robotic manipulator may include a tool drive coupled to a surgical robotic arm that is coupled to a surgical table, and the proximity sensing assembly is coupled to a proximal portion or a distal portion of the tool drive, wherein the proximal portion of the tool drive faces the surgical table during a surgical robotic operation or the distal portion of the tool drive that faces away from the table.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Figure 1:
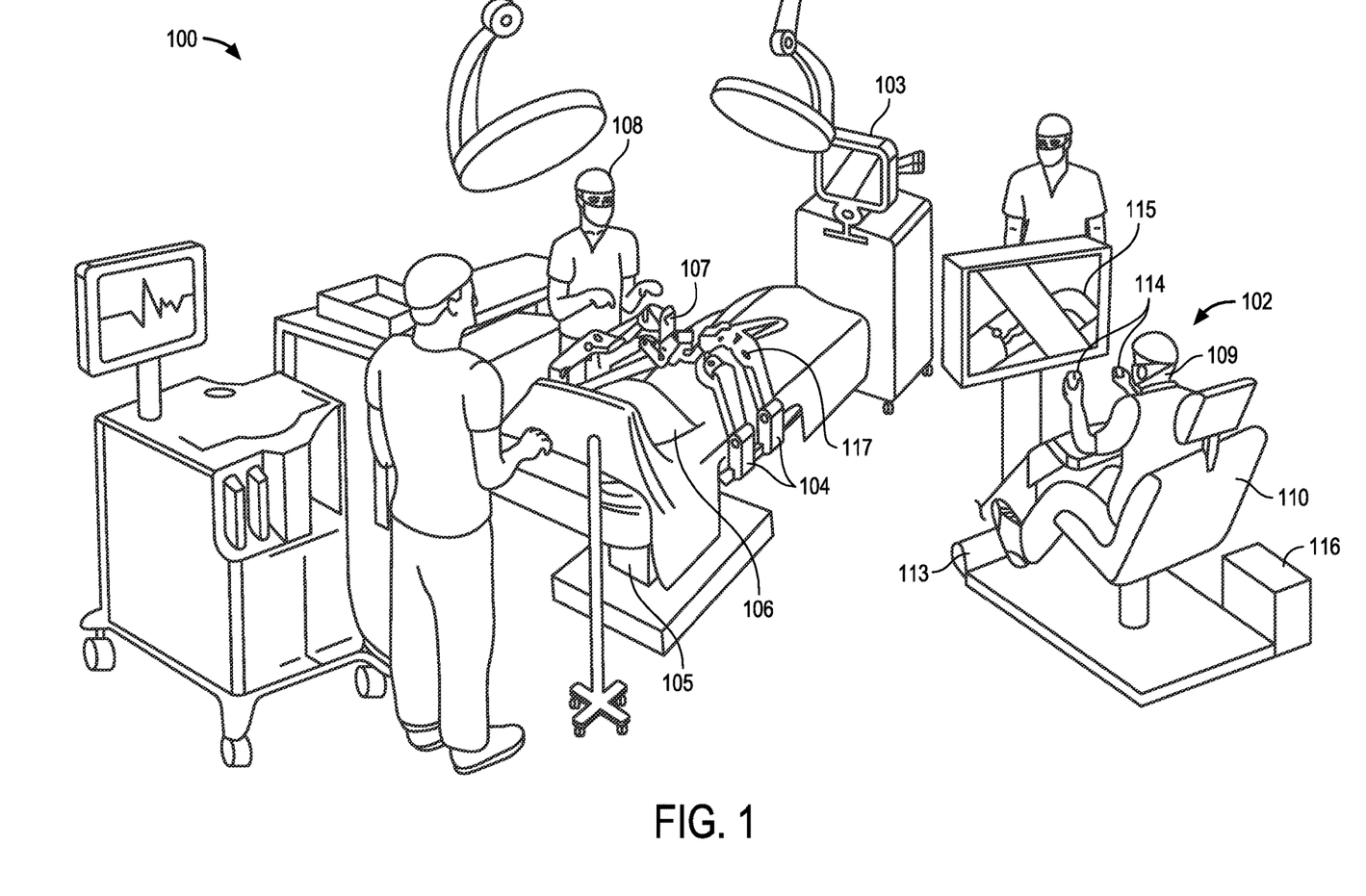
FIG. 1 is a pictorial view of an example surgical robotic system in an operating arena, in accordance with an embodiment.

Referring to FIG. 1, this is a pictorial view of an example surgical robotic system 100 in an operating arena. The surgical robotic system 100 includes a user console 102, a control tower 103, and one or more surgical robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user input devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104.)

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
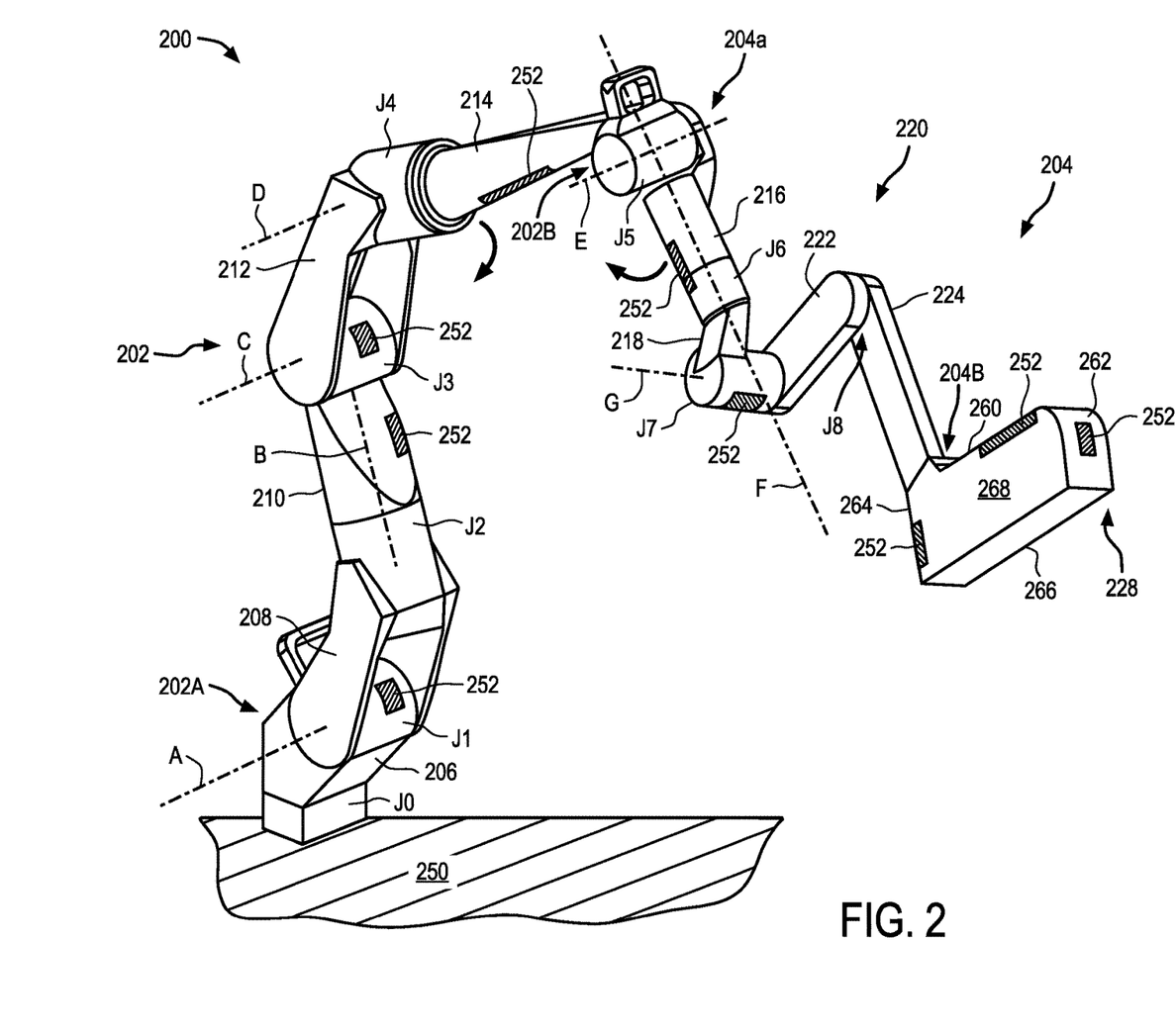
FIG. 2 is a pictorial view of a surgical robotic arm including capacitive hover sensing assemblies, in accordance with an embodiment.

FIG. 2 is a pictorial view of a surgical robotic manipulator including a capacitive hover sensor, in accordance with one embodiment. The surgical robotic manipulator 200 may include a surgical robotic arm having a first section 202 and a second section 204. The first section 202 may include a proximal end 202a and a distal end 202b. The second section 204 may further include a proximal end 204a (e.g., connected to the distal end 202b of first section 202) and a distal end 204b. The surgical robotic manipulator 200 may also include a pitch assembly 220 coupled to a distal end 204b of the second section 204. A tool drive 228 may be coupled to the pitch assembly 220. The tool drive 228 may, or may not be, removable from the pitch assembly 220, and therefore sections 202, 204 making up the surgical robotic arm.

The proximal end 202a of the first section 202 may be coupled to a stationary (or relatively stationary) structure (such as a surgical table) and may be referred to as the first end of the arm 200. The distal end 204b of the second section 204 may be referred to as the second end of the arm 200. Also, the first section 202 may be referred to herein as a "Cartesian arm 202" because (as will be described below) the first section 202 may be used to move the second section 204 into position (e.g., using xyz coordinates in a three dimensional space) at a surgical site on a patient's body. The second section 204 may sometimes be referred to herein as a "spherical arm 204."

The first section 202 includes a first link 206, a second link 208, a third link 210, a fourth link 212, and a fifth link 214. In the embodiments illustrated in FIG. 2, these links are implemented as, and may be referred to herein as a base link 206, a shoulder pitch link 208, a shoulder roll link 210, an elbow link 212, and a forearm link 214. The base link 206 is configured to be removably attached to a structure, such as a surgical table 250. Each link has a proximal end (the end coupled closest to the proximal end 202a of the first section 202) and a distal end (the end coupled furthest from the proximal end 202a), that are coupled to the adjacent structure or link to form a number of joints (e.g., joints J0-J5) which are operable to move the various links with respect to one another, according to a number of degrees of freedom (DOF).

Similarly, the second section 204 includes a first link 216, a second link 218, and a pitch assembly 220. The pitch assembly 220 includes first link 222 and a second link 224. In the embodiments illustrated in FIG. 2, the various links of the second section 204 are implemented as, and may be referred to herein as a spherical arm base link 216, a spherical arm roll link 218, pitch A link 222, and pitch B link 224. Each link is coupled to an adjacent link (or structure) to form a number of joints modules (e.g., joints J5-J7) which allow for movement of one link with respect to another, according to a number of degrees of freedom (DOF). Each of the joints (e.g., J0-J7) may be associated with a motor which drives movement of one link with respect to another along the joint.

Representatively, link 206 may be coupled at its proximal end to a structure such as a surgical table at an initial joint J0, and be associated with a motor (e.g., within the housing of link 206) operable to drive movement of link 206 with respect to the surgical table. Link 208 may be rotatably coupled to link 206 at a first joint J1 having an axis of rotation A ("axis A"), such that the associated motor pivots link 208 about axis A. Link 210 is rotatably coupled to link 208 at a second joint J2 having an axis of rotation B ("axis B"), such that the associated motor causes link 210 to roll about axis B. Link 212 is rotatably coupled to link 210 at a third joint J3 having an axis of rotation C ("axis C"), such that the associated motor causes link 212 to pivot about axis C. Link 214 is rotatably coupled to the link 212 at a fourth joint J4 having an axis of rotation D ("axis D"), such that the associated motor causes link 214 to pivot about axis D. Link 214 (e.g., the most distal link of the first section) may be coupled to link 216 (e.g., the most proximal link of second section 204) at a fifth joint J5 having an axis of rotation E ("axis E"), such that the associated motor causes link 216 (and, consequently, the entire spherical arm 204) to pivot about axis E. Link 216 may be coupled to link 218 at a sixth joint J6 having an axis of rotation F ("axis F"), such that the associated motor causes link 218 to roll about axis F. The pitch assembly 220 (e.g., pitch A link 222) is rotatably coupled to link 218 at a seventh joint J7 having an axis of rotation G ("axis G"), such that the associated motor causes pitch assembly 220 (e.g., pitch A link 222) to pivot about axis G. Pitch assembly 220 may further be considered as having a further joint, for example at eight joint J8, formed by the adjoining links 222, 224, that allows for movement of one of links 222, 224, with respect to another. The tool drive 228 is then coupled to the pitch assembly 220 (e.g., via link 224). The tool drive 228 is configured to engage with a trocar (detachable and replaceable) and manipulate a surgical tool associated therewith (not shown).

As a result of the configuration of links/joints, surgical robotic arm 200 can be manipulated to perform any number of surgical procedures. Such manipulations, however, may also pose risks to objects in the surrounding environment that may be within the range of movement of surgical robotic arm 200. Representatively, during a surgical procedure, a person (e.g., patient, surgeon, assistant, or the like) may have a body part positioned within a range of movement of surgical robotic arm 200. If the person is not aware of the movement of the arm 200 (e.g., an assistant is looking at the display, a patient on the surgical table during surgery, etc.), they may be at risk of getting hit by a portion of arm 200 as it moves from one configuration to another. If the person has their hand or other body part hovering too close to a link (or joint) moving toward another link, their hand (or other body part) could even be pinched between the links. Still further, the object within the range of movement of the surgical robotic arm 200 could be another surgical component that cannot easily avoid, or otherwise move out of the way of, arm 200. For example, the surgical component could be the surgical table 250 the arm 200 is coupled to, or another surgical robotic arm (e.g., see arm 104 of FIG. 1). In addition, collision avoidance can be particularly difficult in a surgical environment where portable surgical components or devices are being used, such as the case here, and there is therefore not a fixed environment that the system can easily control and/or work around.

To avoid collisions between the surgical robotic arm 200 and objects within the surgical arena, surgical robotic arm 200 therefore further includes one or more capacitive hover sensors 252 strategically positioned along collision detection areas or regions of the surgical robotic arm 200. The collision detection areas or regions of the surgical robotic arm 200 are parts of the surgical robotic arm 200 that are likely to contact an unintended object within the surgical arena or would be near an unintended object prior to a collision such that they could be used to detect the collision. In other words, the collision detection areas or regions are not intended to include, for example, portions of surgical robotic arm 200 that a person would intentionally use to control, manipulate, or otherwise move, surgical robotic arm 200.

Figure 3:
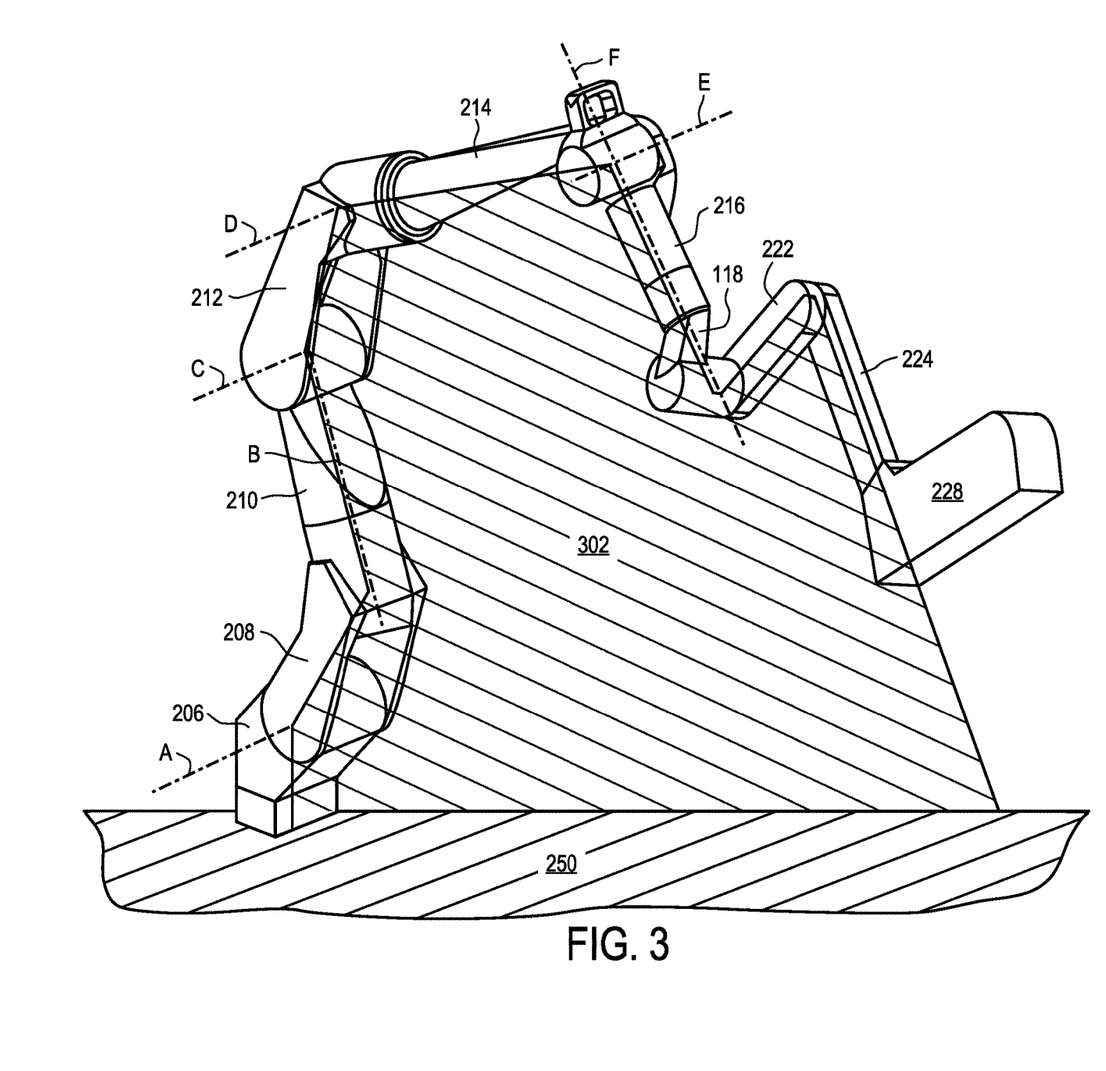
FIG. 3 is a pictorial view of a surgical robotic arm, in accordance with another embodiment.

Representatively, in one aspect, the collision detection areas are surfaces or portions of the housing (e.g., a panel) of surgical robotic arm links 206, 208, 210, 212, 214, 216, 218, pitch assembly links 222, 224 and/or tool drive 228 which could interface with one another when the links bend, fold, collapse, or otherwise articulate, at a joint, and move toward one another such that an object could be unintentionally pinched in between. Representatively, the collision detection areas may be surfaces or portions of robotic arm links 206, 208, 210, 212, 214, 216, 218, pitch assembly links 222, 224 and/or tool drive 228 which face a same direction that the surgical component is moving. For example, the collision detection areas may be curved surfaces or portions of surgical robotic arm links 206, 208, 210, 212, 214, 216, 218, pitch assembly links 222, 224 and/or tool drive 228 which may be considered interior surfaces or portions, or surfaces or portions which are inward to, or bounded by, the link axes A-F. FIG. 3 illustrates a representative interior area 302 considered inward to, bounded by, or generally between, axes A-F and surgical table 250, illustrated in FIG. 3. The terms "interior" or "inward" surface or portion, as used herein, may therefore be intended to refer to a surface or portion of the surgical component that forms an interior angle of the surgical robotic manipulator (e.g. an angle within area 302 bounded by the surgical robotic manipulator and the surgical table). Said another way, the collision detection areas may be curved surfaces or portions of surgical robotic arm links 206, 208, 210, 212, 214, 216, 218, pitch assembly links 222, 224 and/or tool drive 228 which generally face surgical table 250 and/or a patient on table 250 during a surgical procedure.

Returning now to FIG. 2, representative capacitive hover sensing assemblies 252 are shown positioned at collision detection areas at interior surfaces or portions of links 210, 214 and 216. Representatively, link 214 may pivot toward link 210 about joint J3 as shown by the arrow, and link 216 may pivot toward links 210 and/or 214 about joint J5 as shown by the arrow. If a person's hand were positioned near, for example, joint J3, joint J5, and/or any one of links 210, 214 and/or 216 while they are pivoting toward one another, the user's hand could become pinched between the links. One or more capacitive hover sensing assemblies 252 may therefore be positioned at a surface or portion of one or more of moving links 210, 214 and/or 216, that faces the direction of movement so that it can detect that the link 210, 214 and/or 216 is getting closer to the hand and output a signal causing the system to, for example, stop the current movement until the user's hand is no longer detected. Although capacitive hover sensing assemblies 252 are shown at links 210, 214 and 216, it is contemplated that they could be at any collision detection area, interior surface or interior portion of any portion of surgical robotic arm at risk of a collision.

Representatively, in one aspect, the capacitive hover sensing assemblies 252 may be at collision detection areas formed by interior or inwardly facing surfaces or portions of one or more of joints J0-J8. For example, interior surfaces of pivot joints J1, J3 and J7, as shown in FIG. 2, which allow for adjacent links to pivot or rotate toward one another. In this aspect, if a user's hand or other object were positioned near one link which was rotating toward another link, the capacitive hover sensing assembly 252 at the respective joint could detect the hand in between the links, or that the joint was getting closer to the hand, and output a signal causing the system to stop the current movement until the user's hand was no longer detected.

In still further embodiments, it is contemplated that interior (or inward facing) portion, exterior (or outward facing) portions, or a number of other portions of the most distal portion of surgical robotic arm 200 could be at risk of collision since this portion may, at times, be subject to the largest range of movements and/or come near more objects within the surgical arena. Representatively, when surgical robotic arm 200 is, for example, being moved from a stowed configuration to a surgical position, tool drive 228 can experience a relatively large range of movement and may pass by any number of objects within the surgical arena. In addition, tool drive 228 may protrude, or otherwise stick out, farther than the links/joints making up surgical robotic arm 200, making it more susceptible to collision. In addition, since tool drive 228 engages a trocar which in turn engages a surgical tool, tool drive 228 may be relatively close to the patient. Tool drive 228 may therefore have one or more capacitive hover sensing assemblies along an interior housing surface or portion (e.g., a surface facing toward the surgical table and/or within area 302) as previously discussed, an exterior housing surface or portion (e.g., a surface facing away from the surgical table and/or outside of area 302) or any other surface at risk of collision. For example, capacitive hover sensing assemblies 252 may be at the top portion 260 and the distal portion 262 of tool drive 228 as shown in FIG. 2. In this aspect, if a person (e.g., an assistant) is, for example, holding or operating a manual tool at the patient, and therefore near tool drive 228, movement of the tool drive 228 toward the person while they are using the manual tool (or the person toward the tool drive 228) can be detected and a collision prevented. In addition, capacitive hover sensing assemblies 252 may be positioned along a proximal portion 264 of tool drive 228, or any other portion of the tool drive housing which has a direct line to the patient during a surgical procedure, or would otherwise be considered closest to the patient during a surgical procedure. It is contemplated, however, that one or more capacitive hover sensing assemblies may be positioned on other portions of the housing of tool drive 228, for example, the bottom portion 266 or a sidewall 268.

Figure 4:
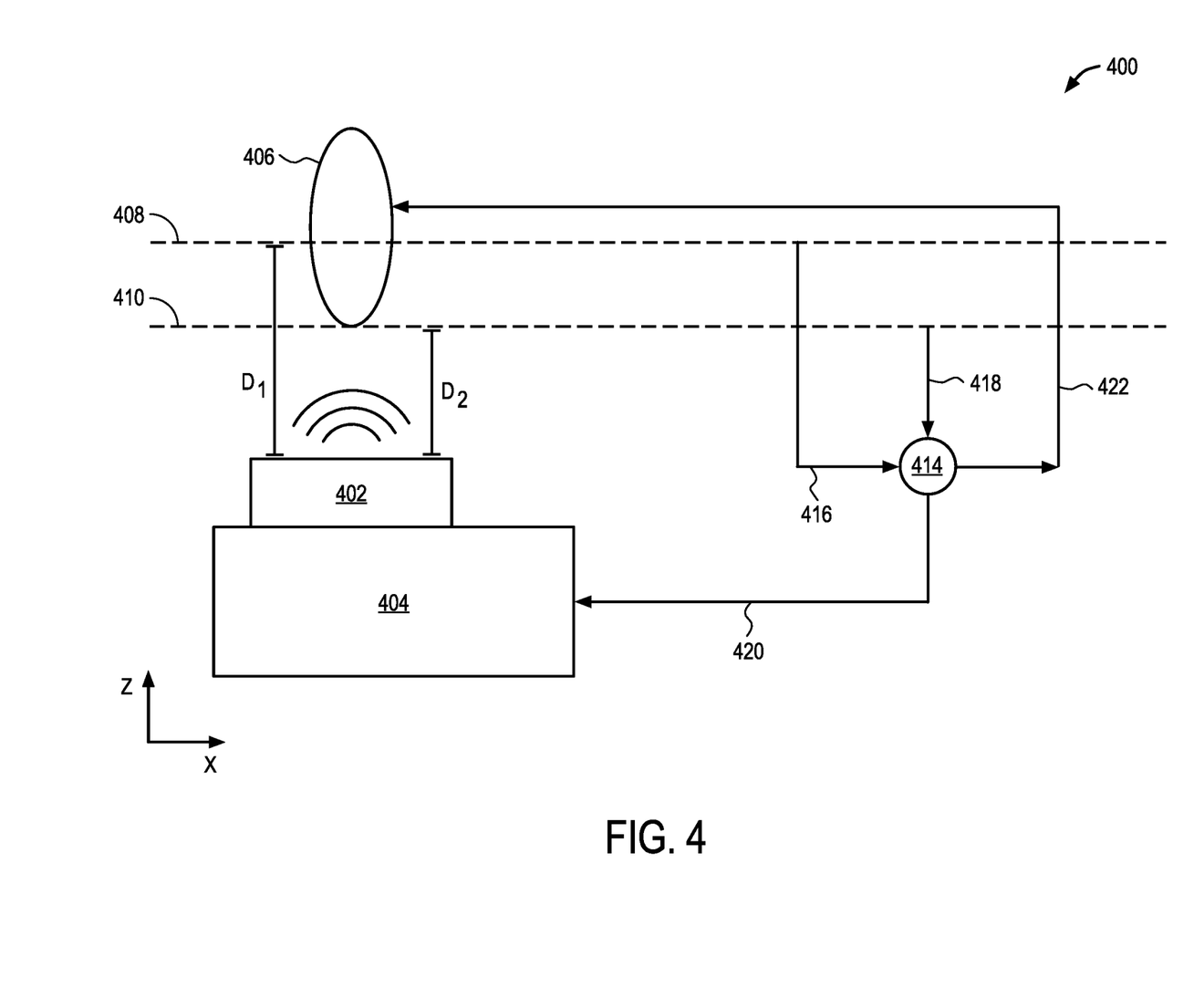
FIG. 4 is a block diagram of an exemplary process for collision prevention of a surgical robotic arm using a capacitive hover sensing assembly, in accordance with an embodiment.

One representative process for detecting an object using a capacitive hover sensing assembly and preventing a collision will now be discussed in reference to FIG. 4. Representatively, FIG. 4 illustrates a capacitive hover sensing system 400 including a capacitive hover sensing assembly 402 coupled to a surgical robotic arm 404. The capacitive hover sensing assembly 402 may include one or more capacitive pads, lines, regions or the like, made of any sort of conductive material that allows for capacitive sensing of an object near the sensor without any portion of the object physically touching the sensor. Representatively, each of the capacitive members may be made of a copper material that is formed on, in, or otherwise coupled to the surgical robotic arm 404. Application of a voltage to the capacitive members results in the formation of an electrostatic field at each of the capacitive members. When an object that is conductive or has a dielectric constant different than air, for example any portion of a user's hand, is brought in close proximity to the capacitive members, it changes the local electric field, and in turn the capacitance at each of members. This change in capacitance can be detected by assembly 402 and output as a sensor signal to a controller/processor 414 to determine/measure the proximity, location, position, displacement, movement or the like, of object 406 with respect to assembly 402, and surgical robotic arm 404. The controller/processor 414 can, in turn, send a robotic control signal to the surgical robotic arm 404 causing it to, for example, stop moving, so that a collision is avoided.

Referring now in more detail to the capacitive hover sensing system 400 illustrated in FIG. 4, it can be seen that system 400 includes a collision avoidance range 408, which corresponds to a desired minimum spacing to be maintained between surgical robotic arm 404 and object 406 to avoid a collision. The collision avoidance range 408 may be a predetermined or calibrated range that is programmed into system 400. System 400 further includes an actual object range 410, which corresponds to an actual spacing between surgical robotic component 404 and a detected object 406. Capacitive hover sensing assembly 402 is configured to output signals, for example output signal 418, corresponding to these detection parameters that can be used to determine whether the desired spacing between object 406 and surgical robotic component 404 to avoid a collision is met. Representatively, when an object 406 is placed over assembly 402, sensing assembly 402 detects the presence of the object 406 as a change in capacitance at any one or more of the associated capacitive members, and this change in capacitance is sent as a corresponding output signal 418 to system controller 414, which in turn, uses this information to determine (e.g., measure) the actual distance (D2) between object 406 and sensing assembly 402. A collision avoidance distance (D1), which corresponds to the minimum distance required to avoid a collision, is then compared, by the controller 414, to the actual distance (D2). The collision avoidance distance (D1) may be a predefined fixed value or value range 416, which represents the avoidance range 408 in the sensing coordinates/measurement system. This value or range 416 may be kept fixed or dynamically modulated throughout the operation, for example, depending on the measured robot movement speed. Value or range 416, corresponding to distance (D1), may be input to, and/or stored by, controller 414. When it is determined that the actual object distance (D2) is the same as or less than collision avoidance distance (D1), the system determines a collision is imminent (or has occurred) and enters a collision avoidance mode. In this mode, controller 414 sends a robotic command signal 420 to surgical robotic arm 404 causing the surgical robotic arm 404 to engage in a collision avoidance operation. The collision avoidance operation may be, for example, to stop moving, change trajectory, or engage in some other motion, which will avoid a collision. In addition, since it is further known which link/joint of surgical robotic arm 404 the sensing assembly 402 is at, in addition to being able to determine the proximity of object 406 to surgical robotic arm 404, system 400 can determine the approximate location of the collision, and also use the collision location information to determine the appropriate collision avoidance operation to avoid the collision. For example, if the object 406 is detected near a sensing assembly 402 at a link near a proximal end of the surgical robotic arm 404 (e.g., one of links 206, 208, 210, 212 of FIG. 2) but not a link at a distal end of the surgical robotic arm 404 (e.g., one of links 214, 216, 218), the system 400 determines the collision is likely to occur near the proximal end of the surgical robotic arm 404 and determines an appropriate avoidance operation accordingly. On the other hand, when it is determined that the actual object distance (D2) is greater than collision avoidance distance (D1), the system determines the object is a safe distance from surgical robotic arm 404 and collision avoidance operations are unnecessary (e.g., surgical robotic arm 404 may remain in its current operation mode).

In still further embodiments, it is contemplated that when the object 406 is a component of the surgical robotic system, for example another surgical robotic arm (e.g., see surgical robotic arms 104 of FIG. 1), surgical table, a tool, etc., a robotic command signal 422 may be sent to the object 406 instead of, or in addition to, surgical robotic arm 404 to cause the object to engage in a collision avoidance operation. The collision avoidance operation may cause the object 406 to, for example, reposition itself, change trajectory, or engage in some other movement that will avoid a collision. For example, the position and/or trajectory of the movement of surgical robotic arm 404 within the surgical arena is known by controller 414. Thus, when another surgical robotic arm is detected as being in the way of surgical robotic arm 404, system 400 may output a robotic command signal 422 to the other surgical robotic arm causing it to be reconfigured or otherwise move so that it is outside of the trajectory of the movement of surgical robotic arm 404. In addition, controller 414 may cause any number of objects that are detected as being in the pathway of surgical robotic arm 404 to be moved or otherwise reconfigured to avoid a collision.

Moreover, in addition to, or instead of, automatically causing the surgical robotic arm 404, object 406 or another object within the surgical arena to engage in a collision avoidance operation once an imminent collision is detected, controller 414 may initiate an alarm (e.g., audio, haptic, or the like) to alert the user that a collision is imminent. The user may then determine the best course of action to avoid the collision. For example, the alarm may be an audible alarm which sufficiently alerts the user that they may have a body part about to get pinched between links of the surgical robotic arm 404, and based on this alert, the user may move their body part to avoid the collision without interrupting any robotic operations the system is engaging in.

Figure 5:
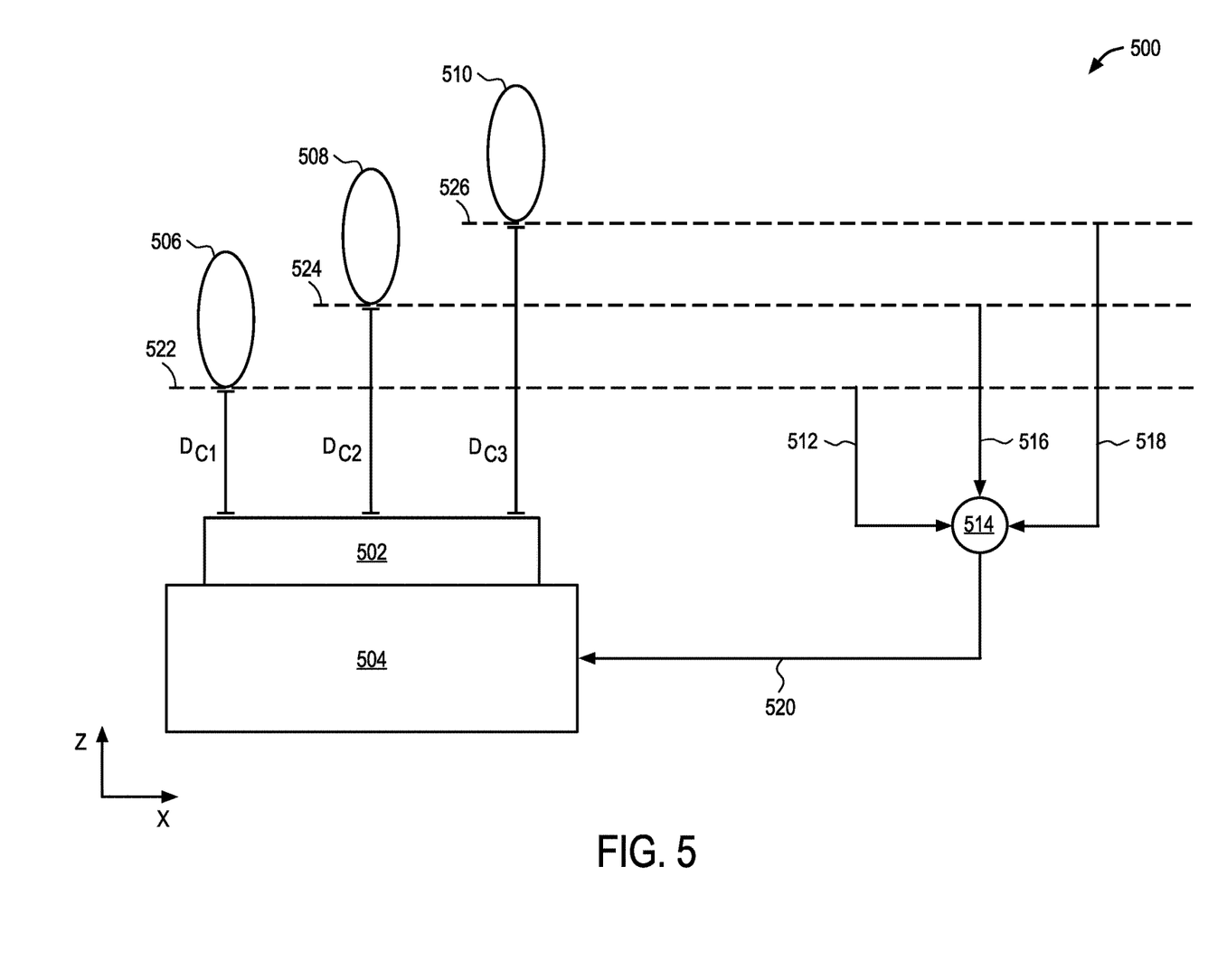
FIG. 5 is a block diagram of an exemplary process for collision prevention of a surgical robotic arm using a capacitive hover sensing assembly, in accordance with an embodiment.

It is further contemplated that in some embodiments, in addition to detecting the presence and location of the object relative to surgical robotic arm, the capacitive hover sensing assembly can be used to determine the type of object, and a sensitivity of the capacitive hover sensing assembly and/or response of the overall system tuned depending on the type of object. One representative system for detecting a type of object using a capacitive hover sensing assembly and preventing a collision will now be discussed in reference to FIG. 5. Representatively, similar to FIG. 4, FIG. 5 shows system 500 including a capacitive hover sensing assembly 502 coupled to a surgical robotic arm 504, and a controller 514 for receiving signals 512, 516 and 518 from the sensing assembly 502 and outputting a corresponding robotic command signal 520 to surgical robotic arm 504. In this embodiment, however, there are a number of collision avoidance ranges 522, 524, 526, which vary depending on the type of object 506, 508 or 510 that is detected by capacitive hover sensing assembly 502. Representatively, in some cases, a collision with one object may be more dangerous, create more risk within the overall system or otherwise be more necessary to prevent, than a collision with another object. For example, a collision with the patient may be considered more dangerous, as creating more risk and/or more necessary to prevent, than a collision with the surgical table or another object that can be moved out of the way (e.g., another surgical robotic arm). System 500 may therefore also be configured to determine the type of object and be more sensitive to a collision with an object determined to be at higher safety risk than one determined to be a lower safety risk. The type of object can be determined based on its capacitive value, as detected by capacitive hover sensing assembly 502. In particular, objects made of different materials will have different capacitance values. For example, the capacitance value corresponding to a metal surface will be higher than a capacitance value corresponding to a person. Accordingly, where object 506 includes a first material, object 508 includes a second material and object 510 is includes a third material, they will each have different capacitance values C1, C2 and C3, respectively. These different capacitance values C1, C2 and C3 can be determined by controller 514 from the sensing assembly 503 output signals 512, 516 and 518. Controller 514 is further programmed to determine the object (or likely object) depending on the capacitance value C1, C2 or C3 that is detected. For example, capacitance value C1 may be high and therefore determined to correspond to an object including a metal material, for example, a metal surgical table. Capacitance value C3 may be low and therefore determined to correspond to an object that is a person. Capacitance value C2 may be somewhere in between C1 and C3 and therefore determined to correspond to an object such as a surgical robotic arm which could include materials having a capacitance value somewhere in between metal and a person.

The collision sensitivity and/or response of system 500 can further be tuned depending on the object. For example, FIG. 5 illustrates a sensitivity of system 500 tuned according to three different types of objects 506, 508 and 510. Representatively, system 500 is shown as being least sensitive to collision with object 506 (e.g., least collision risk), more sensitive to collision with object 508 (e.g., more collision risk) and most sensitive to collision with object 510 (e.g., most collision risk). For example, when object 510 determined to be a person (e.g., a low capacitance value C3 is detected), system 500 will want to enter a collision mode and engage in collision preventive actions sooner than in the case of object 508 determined to be a surgical table (e.g., higher detected capacitance value C2) or object 506 determined to be a surgical robotic arm (e.g., higher detected capacitance value C1). Thus, the collision avoidance mode for object 510 (e.g., a patient) is triggered when object 510 is sensed at a collision avoidance range 526 (e.g., the desired minimum spacing to avoid a collision) which is set at a relatively large distance (DC3) from sensing assembly 502. On the other hand, the collision avoidance mode for object 506 (e.g., a surgical robotic arm) and object 508 (e.g., a surgical table) may be triggered at collision avoidance ranges 522 and 524, which are set at shorter distances (DC1) and (DC2), respectively, from sensing assembly 502. In other words, surgical robotic arm 404 can be closer to objects 506 and 508, than object 510, before triggering the collision avoidance mode and any collision avoidance operations. This can be the case because, as previously discussed, the level of risk is considered lower when surgical robotic arm 504 is in close proximity to an inanimate object (i.e., not a person) and/or another surgical robotic component (e.g., a surgical robotic arm or surgical table) which can itself be moved or reconfigured to avoid a collision, than when it is about to collide with a person. For example, the surgical robotic arm can be reconfigured so that it can now reach desired locations within the patient without hitting the table or the patient. Still further, similar to system 400, system 500 may be configured to instead or, or in addition to, sending a robotic command signal to surgical robotic arm 504, send a robotic command signal to the other surgical robotic component or other component within the surgical arena, to cause that component to engage in a collision avoidance operation (e.g., move, reposition itself, etc). Moreover, as previously discussed, in addition to, or instead of, automatically causing one of the surgical robotic components to engage in a collision avoidance operation once an imminent collision is detected, system 500 may initiate an alarm (e.g., audio, haptic, or the like) to alert the user that a collision is imminent. For example, where it is determined that the object is a person that is assisting in the operation (e.g., the person is detected near the distal end of the tool drive), an audible alarm may be all that is necessary to alert the user to move their body part to avoid the collision without interrupting any robotic operations the system is engaging in.

Figure 6:
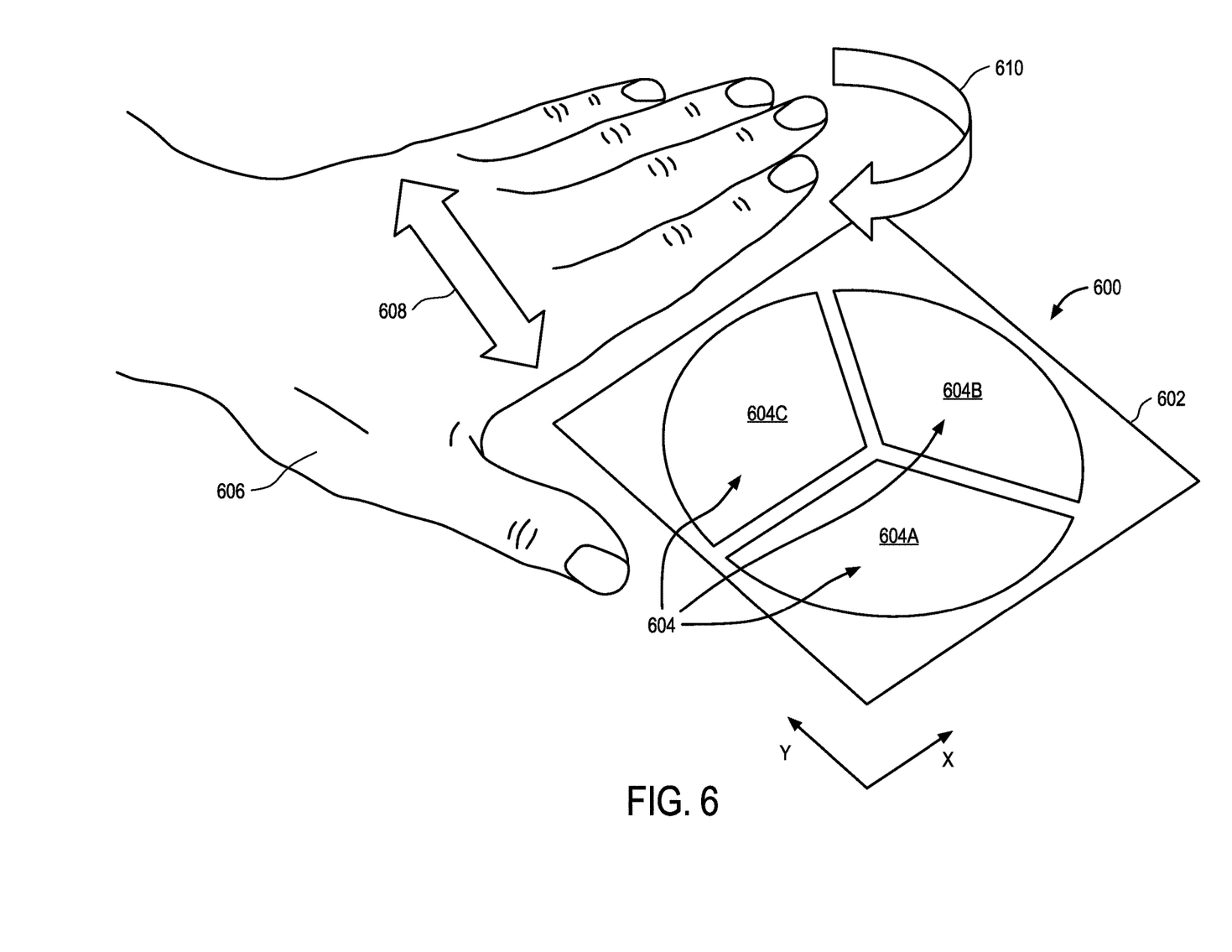
FIG. 6 is a pictorial view of an exemplary capacitive hover sensing assembly, in accordance with an embodiment.

Referring now in more detail to the capacitive hover sensing assembly, FIG. 6 illustrates one representative embodiment of a capacitive hover sensing assembly that may be incorporated into any one or more of the previously discussed systems or components. Capacitive hover sensing assembly 600 may include a support member 602 and an arrangement of capacitive members 604. Capacitive members 604 may be made of any sort of conductive material that allows for capacitive sensing of an object near the sensor without any portion of the object physically touching the sensor. Capacitive members 604 may be referred to herein as capacitive pads, capacitive regions, capacitive lines, or the like, depending on their particular size, shape and/or configuration with respect to the support member. Representatively, each of capacitive members 604 may be made of a copper material that is formed on, in, or otherwise coupled to support member 602, which can be any structure made of an insulating material (e.g., plastic, ceramic, etc.). Application of a voltage to the capacitive members 604 results in the formation of an electrostatic field at each of the capacitive members 604. When an object 606 that is conductive or has a dielectric constant different than air, for example any portion of a user's hand, is brought in close proximity to the capacitive members 604, it changes the local electric field, and in turn the capacitance at each of members 604. This change in capacitance at each of the capacitive members 604 can be sensed by assembly 600 and output as a sensor signal to a controller/processor of surgical robotic system 100 to determine/measure the capacitance, proximity, location, position, displacement, movement or the like, of object 606 with respect to assembly 600, and any surgical robotic component that sensor assembly 600 is coupled to. The controller/processor can, in turn, cause the associated surgical robotic component to engage in a collision avoidance operation, without direct contact between the object 606 and the component.

In this embodiment, capacitive members 604 are arranged in a pie pattern that allows for the detection of both a linear movement and an angular movement of the object 606. For example, a linear movement of object 606 is illustrated by arrow 608 and an angular movement is illustrated by arrow 610. In this aspect, capacitive members 604 may include capacitive members 604A, 604B and 604C which are each formed as substantially triangular shaped pieces that together make up a circular capacitive hover sensing region. Each of capacitive members 604A-604C may be made of a conductive material, which as previously discussed, can form an electrostatic field at each of the capacitive members 604A-604C upon application of a voltage. When object 606 is brought in close proximity to the capacitive members 604A-604C, it changes the local electric field, and in turn, the capacitance at each of members 604A-604C. This change in capacitance at each of the capacitive members 604A-604C can be used to determine a linear movement 308 and/or an angular motion 610 of object 606, without object 606 physically touching the component. For example, a hovering of object 606 over capacitive members 604A, 604C may initially be detected, followed by a hovering of object 606 over capacitive members 604A, 604B. This may occur, for example, where initially the user's palm is positioned over capacitive member 604A and the fingers are positioned over capacitive member 604C, and the user then rotates their hand to the right as shown by arrow 610 (in the x-y plane) so that while the palm remains over capacitive member 604A, the fingers are now over capacitive member 604B and not member 604C. Capacitive hover sensing assembly 600 may detect such a movement as, for example, an initial change in capacitance at members 604A, 604C, followed by a change in capacitance at member 604B, and member 604C returning to its initial state. A corresponding signal(s) may be output by capacitive hover sensing assembly 600 to the surgical robotic system controller/processor for determining whether object 606 is too close and collision avoidance operations are necessary.

It should further be understood that, in some embodiments, the sensing assembly 600 may be integrated into any one or more of the surgical robotic components discussed herein. For example, the capacitive member(s) may be made of a conductive material that is printed directly onto a surface (i.e., support member) of a surgical robotic arm (e.g., surgical robotic arms 104 or 200) into the desired arrangement or pattern, or etched into a surface of the surgical robotic component. The surface could be any surface or portion of the surgical robotic component that is at risk of collision, as previously discussed. For example, where the surgical robotic component is surgical robotic arm 200, the surface may be a collision detection area, region or portion of a cosmetic panel or outer shell of the surgical robotic arm link or joint. Still further, where the surgical robotic component is the surgical table, the surface may be a collision detection area or region of a cosmetic panel along a side of the surgical table. In some aspects, the support member forms the cosmetic panel or outer shell of the surgical robotic component. It should therefore be understood that sensing assembly 600 is not intended to be limited to a flat plane, or any other shape/size, rather it can be formed or manufactured to have any size and shape suitable for use with any surgical robotic system component.

Figure 7:
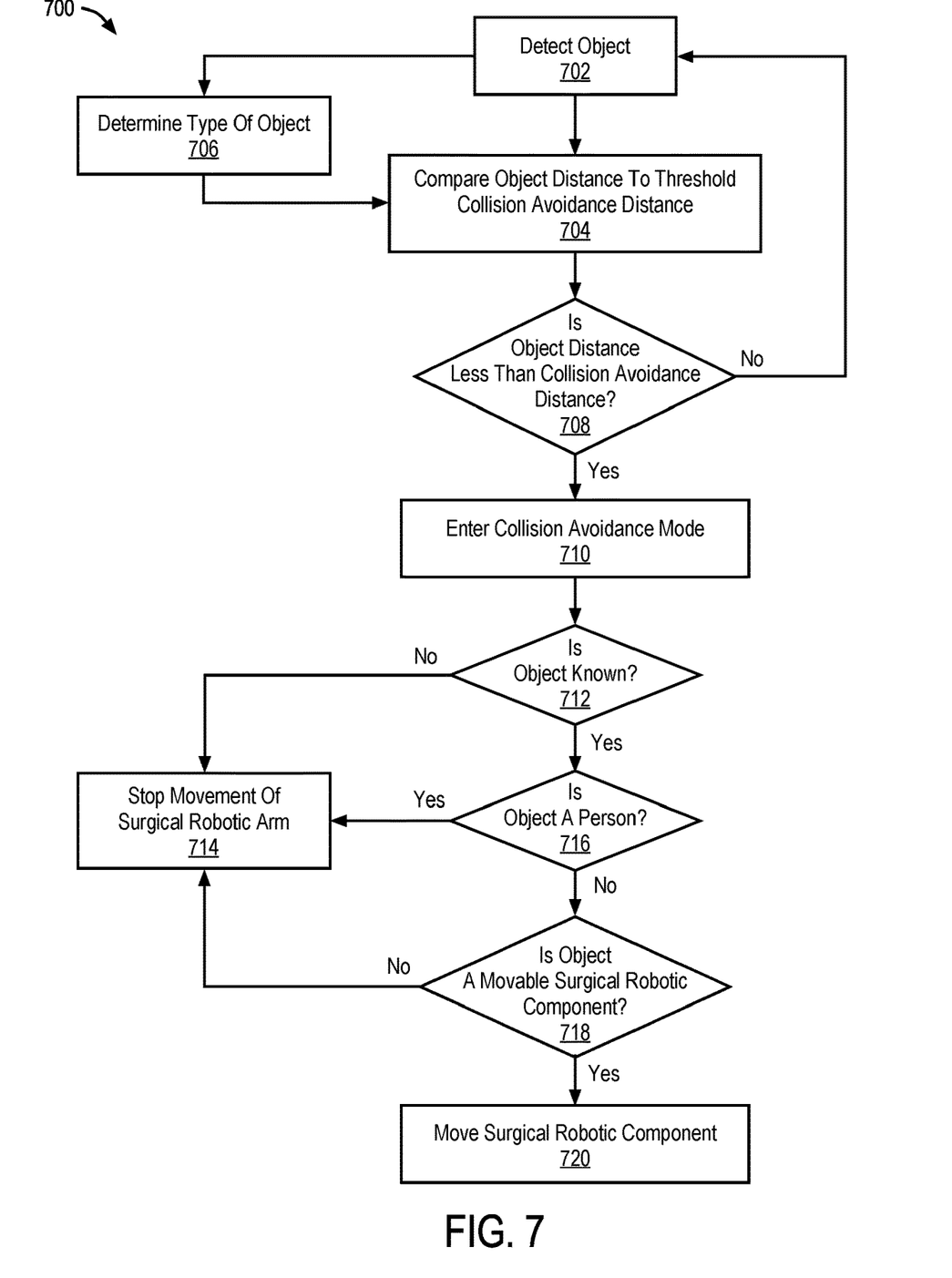
FIG. 7 is a block diagram of an exemplary process for collision prevention of a surgical robotic arm using a capacitive hover sensing assembly, in accordance with an embodiment.

FIG. 7 illustrates a block diagram of one representative collision avoidance process, according to one embodiment. Process 700 includes operation 702 of detecting an object. The object may be detected using a capacitive hover sensing assembly as previously discussed herein. Once an object is detected, the object distance may be compared to a threshold collision avoidance distance (operation 704) and then the two distances compared to determine whether the object distance is less than the collision avoidance distance (operation 708). In addition, process 700 may include the additional operation of determining the type of object as previously discussed in connection with FIG. 5 (operation 704). If the object distance is not less than the collision avoidance distance, process 700 returns to operation 702 and continues the object detection operation. If the object distance is less than the collision avoidance distance, the system enters a collision avoidance mode (operation 710). It should further be recognized that in some embodiments, an object distance equal to the collision avoidance mode distance may further cause entry to the collision avoidance mode. In the collision avoidance mode 710, the process considers whether the type of object is known at operation 712 (e.g., as determined by operation 706). If the object type is not known, a command to stop movement of the surgical robotic arm is issued causing the surgical robotic arm to stop moving (operation 714). If the object type is known and the object is a person (operation 716), the process returns to operation 714 to initiate a command to stop movement of the surgical robotic arm causing the surgical robotic arm to stop moving. If the object is not a person, process 700 continues to operation 718 to determine whether the object is a movable surgical robotic component (e.g., another surgical robotic arm). If it is not a movable component (e.g., surgical table connected to the surgical robotic arm), the process returns to operation 714 to initiate a command to stop movement of the surgical robotic arm causing the surgical robotic arm to stop moving. If, however, the object is a movable surgical robotic component, the process continues to operation 720 and initiates a command to move, reconfigure, reposition the movable component to a non-collision location so that the surgical robotic arm does not collide with the movable surgical robotic component. Alternatively, or in addition to, any of the above operations once an object is detected, the system may initiate an alert, such as an audible alarm or haptic response, to alert the use of an imminent collision. It should be understood that while the operations of process 700 are described in one particular, order, they may be performed in any order and in combination to avoid collision of a surgical robotic arm with an object.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A collision avoidance method for a surgical robotic manipulator, the method comprising:
   detecting a distance of an object to the surgical robotic manipulator using a proximity sensing assembly coupled to at least one of a plurality of links or a plurality of joints of the surgical robotic manipulator;
   determining whether a collision between the object and the surgical robotic manipulator is imminent by comparing the detected distance of the object to a predetermined collision avoidance distance;
   determining whether the object is a human obstacle based on a capacitance value change detected by the proximity sensing assembly that is lower than a capacitance value change detected by the proximity sensing assembly when the object is a non-human obstacle; and
   based on the determining of an imminent collision and the object is a human obstacle, causing the surgical robotic manipulator to engage in a collision avoidance operation that prevents the surgical robotic manipulator from colliding with the human obstacle.

2. The method of claim 1 wherein the collision avoidance operation comprises terminating movement of the surgical robotic manipulator.

3. The method of claim 1 further comprising determining the object is a non-human obstacle based on the capacitance value change detected by the proximity sensing assembly, and determining a type of non-human obstacle.

4. The method of claim 3 determining the type of non-human obstacle is another surgical robotic manipulator and terminating movement of the another surgical robotic manipulator.

5. The method of claim 3 wherein the predetermined collision avoidance distance is different depending on whether the object is a human obstacle or a non-human obstacle.

6. The method of claim 1 further comprising determining a location of the human obstacle with respect to a particular one of the plurality of links using the proximity sensing assembly, and based on the distance of the human obstacle and the location of the human obstacle to the surgical robotic manipulator, determining the collision avoidance operation.

7. The method of claim 1 wherein at least one of the plurality of links is operable to move in a first direction, and the proximity sensing assembly is coupled to a curved portion of the at least one of the plurality of links that faces the first direction.

8. The method of claim 1 wherein the surgical robotic manipulator comprises a surgical robotic arm comprising at least seven links and at least seven joints that cause the at least seven links to move with respect to one another, and the proximity sensing assembly is coupled to a portion of a first link that faces a second link when the first link pivots about a first joint.

9. The method of claim 1 wherein the surgical robotic manipulator comprises a tool drive coupled to a surgical robotic arm that is coupled to a surgical table, and the proximity sensing assembly is coupled to a proximal portion or a distal portion of the tool drive, wherein the proximal portion of the tool drive faces the surgical table during a surgical robotic operation or the distal portion of the tool drive that faces away from the table.

10. The method of claim 1 wherein the predetermined collision avoidance distance corresponds to a predetermined distance to be maintained between the human obstacle and the surgical robotic manipulator to avoid a collision.

11. The method of claim 1 wherein the proximity sensing assembly is coupled to a portion of at least one of the plurality of links that faces another link of the plurality of links when the surgical robotic manipulator is moving.

12. A collision avoidance method for a surgical robotic system, the method comprising:
   determining a first capacitance value detected by a hover sensing assembly corresponds to a human object by comparing the first capacitance value to a second capacitance value corresponding to a non-human object and determining the first capacitance value is lower than that of the non-human object;
   detecting a distance of the human object to a surgical robotic manipulator using the hover sensing assembly, wherein the surgical robotic manipulator comprises a plurality of links coupled together by a plurality of joints that are operable to move with respect to one another to move the surgical robotic manipulator and the hover sensing assembly is coupled to a portion of at least one of the plurality of links that faces another link of the plurality of links when the surgical robotic manipulator is moving;
   determining whether a collision between the human object and the surgical robotic manipulator is imminent by comparing the detected distance of the human object to a predetermined collision avoidance distance, the predetermined collision avoidance distance corresponding to a predetermined distance to be maintained between the human object and the surgical robotic manipulator to avoid a collision; and
   based on the determining that the collision is imminent, transitioning the surgical robotic system to a collision avoidance mode to prevent the surgical robotic manipulator from colliding with the human object.

13. The method of claim 12 wherein the collision avoidance mode comprises terminating movement of the surgical robotic manipulator.

14. The method of claim 12 further comprising determining a location of the human object with respect to a particular one of the plurality of links coupled together by a plurality of joints using the hover sensing assembly, and based on the distance of the human object and the location of the human object to the surgical robotic manipulator, determining a collision avoidance operation in the collision avoidance mode.

15. The method of claim 12 wherein at least one of the plurality of links is operable to move in a first direction, and the hover sensing assembly is coupled to a portion of the at least one of the plurality of links that faces the first direction.

16. The method of claim 12 wherein the hover sensing assembly is coupled to a portion of at least one of the plurality of links or at least one of the plurality of joints that forms an interior angle of the surgical robotic manipulator.

17. The method of claim 12 wherein the hover sensing assembly comprises a capacitive sensor.

18. The method of claim 17 wherein the capacitive sensor comprises a conductive material formed on a curved surface of at least one of the plurality of links or at least one of the plurality of joints.

19. The method of claim 12 wherein the method further comprising detecting the second capacitance value corresponding to the non-human object and a distance of the non-human object to the surgical robotic manipulator using the hover sensing assembly, and wherein the collision avoidance mode comprises terminating movement of the non-human object to prevent the non-human object from colliding with the surgical robotic manipulator.

* * * * *